United States Patent
Warren et al.

(10) Patent No.: US 8,795,716 B2
(45) Date of Patent: *Aug. 5, 2014

(54) SKIN CARE COMPOSITIONS ON A THIN SANITARY NAPKIN

(75) Inventors: Raphael Warren, Amberly Village, OH (US); John Lee Hammons, Hamilton, OH (US); John Michael Blevins, Cincinnati, OH (US); Thomas James Klofta, Cincinnati, OH (US); Ryo Minoguchi, Blue Ash, OH (US); Regina Leigh Pennington, Cincinnati, OH (US); James Anthony Staudigel, Cincinnati, OH (US); Paul Robert Tanner, Lebanon, OH (US); Michael Lee Vatter, Okeana, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1738 days.

This patent is subject to a terminal disclaimer.

(21) Appl. No.: 10/992,430

(22) Filed: Nov. 18, 2004

(65) Prior Publication Data

US 2005/0148962 A1 Jul. 7, 2005

Related U.S. Application Data

(63) Continuation-in-part of application No. 10/152,924, filed on May 21, 2002, now abandoned, which is a continuation-in-part of application No. 09/968,154, filed on Oct. 1, 2001, now abandoned.

(60) Provisional application No. 60/581,483, filed on Jun. 21, 2004.

(51) Int. Cl.
*A61F 13/15* (2006.01)
*A61K 8/00* (2006.01)

(52) U.S. Cl.
USPC .......... 424/443; 604/358; 604/361; 604/362; 424/401; 424/402

(58) Field of Classification Search
CPC . A61F 13/511; A61F 13/514; A61F 13/4704; A61F 13/47; A61F 13/5616
See application file for complete search history.

(56) References Cited

U.S. PATENT DOCUMENTS

| 3,489,148 | A | 1/1970 | Duncan et al. |
| 3,896,807 | A | 7/1975 | Buchalter |

(Continued)

FOREIGN PATENT DOCUMENTS

| CA | 2024558 | * | 4/2002 |
| DE | 108036 | | 9/1974 |

(Continued)

OTHER PUBLICATIONS

PCT International Search Report dated Apr. 2, 2003.

*Primary Examiner* — Lakshmi Channavajjala
(74) *Attorney, Agent, or Firm* — Andres E. Velarde; Amanda T. Barry; Jason J. Camp

(57) ABSTRACT

Disclosed is a sanitary napkin for wearing adjacent the pudendal region, the sanitary napkin having a skin care composition applied thereon, wherein the sanitary napkin has a caliper less than about 5.0 mm. The skin care composition can have from about 0.001% to about 0.1% by weight of hexamidine, from about 0.001% to about 10% by weight of zinc oxide, from about 0.01% to about 10% by weight of niacinamide, and a carrier.

20 Claims, 4 Drawing Sheets

(56) References Cited

U.S. PATENT DOCUMENTS

| | | |
|---|---|---|
| 4,911,932 A | 3/1990 | Clum |
| 5,180,620 A | 1/1993 | Mende |
| 5,445,823 A | 8/1995 | Hall |
| 5,607,760 A | 3/1997 | Roe |
| 5,609,587 A | 3/1997 | Roe |
| 5,635,191 A | 6/1997 | Roe et al. |
| 5,643,588 A | 7/1997 | Roe et al. |
| 5,968,025 A | 10/1999 | Roe et al. |
| 6,107,537 A | 8/2000 | Elder et al. |
| 6,118,041 A | 9/2000 | Roe et al. |
| 6,149,924 A | 11/2000 | Paul |
| 6,153,209 A * | 11/2000 | Vega et al. .............. 424/404 |
| 6,160,200 A * | 12/2000 | Ehrnsperger et al. ........ 604/378 |
| 6,217,890 B1 | 4/2001 | Paul |
| 6,426,444 B2 | 7/2002 | Roe et al. |
| 6,497,893 B1 | 12/2002 | Everhart et al. |
| 6,503,524 B1 | 1/2003 | Tyrrell et al. |
| 6,548,158 B2 * | 4/2003 | Mizutani et al. ............ 428/323 |
| 6,586,652 B1 | 7/2003 | Roe et al. |
| 6,703,536 B2 * | 3/2004 | Roe et al. .................. 604/360 |
| 6,706,946 B1 | 3/2004 | Lankhof et al. |
| 6,716,441 B1 * | 4/2004 | Osborne et al. ............ 424/404 |
| 6,825,393 B2 | 11/2004 | Roe et al. |
| 6,861,571 B1 | 3/2005 | Roe et al. |
| 7,172,801 B2 * | 2/2007 | Hoying et al. .............. 428/92 |
| 7,270,861 B2 * | 9/2007 | Broering et al. ............ 428/35.7 |
| 7,410,683 B2 * | 8/2008 | Curro et al. ................ 428/133 |
| 7,507,459 B2 * | 3/2009 | Turner et al. ............... 428/88 |
| 7,553,532 B2 * | 6/2009 | Turner et al. ............... 428/133 |
| 7,648,732 B2 * | 1/2010 | Ott et al. .................... 427/193 |
| 7,670,665 B2 * | 3/2010 | Hoying et al. .............. 428/133 |
| 7,682,686 B2 * | 3/2010 | Curro et al. ................ 428/172 |
| 7,732,657 B2 * | 6/2010 | Hammons et al. ........... 604/358 |
| 7,785,690 B2 * | 8/2010 | Turner et al. ............... 428/97 |
| 7,829,173 B2 * | 11/2010 | Turner et al. ............... 428/92 |
| 7,838,099 B2 * | 11/2010 | Curro et al. ................ 428/96 |
| 7,938,635 B2 * | 5/2011 | Heilman et al. ............. 425/101 |
| 8,075,977 B2 * | 12/2011 | Curro et al. ................ 428/92 |
| 8,153,225 B2 * | 4/2012 | Turner et al. ............... 428/88 |
| 2003/0082219 A1 | 5/2003 | Warren et al. |
| 2003/0206943 A1 | 11/2003 | Hammons et al. |
| 2004/0170589 A1 | 9/2004 | Gatto |
| 2005/0129651 A1 | 6/2005 | Gatto et al. |
| 2005/0154362 A1 | 7/2005 | Warren et al. |
| 2006/0062816 A1 | 3/2006 | Gatto et al. |
| 2007/0286876 A1 | 12/2007 | Warren et al. |

FOREIGN PATENT DOCUMENTS

| | | |
|---|---|---|
| DE | 3444464 A1 | 1/1986 |
| DE | 41 36 540 A1 | 5/1992 |
| DE | 4401308 A1 | 7/1995 |
| EP | 0 095 615 A2 | 12/1983 |
| EP | 737462 A1 * | 10/1996 |
| EP | 0 769 291 A1 | 4/1997 |
| EP | 1 051 958 A1 | 11/2000 |
| WO | WO 9515138 | 6/1995 |
| WO | WO 97/17060 A1 | 5/1997 |
| WO | WO 99/18919 A2 | 4/1999 |
| WO | WO 99/45973 A1 | 9/1999 |
| WO | WO 99/45974 A1 | 9/1999 |
| WO | WO 99/53907 A2 | 10/1999 |
| WO | WO 99/55303 A1 | 11/1999 |
| WO | WO 00/01351 A1 | 1/2000 |
| WO | WO 00/10500 A1 | 3/2000 |
| WO | WO 00/27191 A1 | 5/2000 |
| WO | WO 00/48544 A1 | 8/2000 |
| WO | WO 00/69485 | 11/2000 |
| WO | WO 00/69485 A1 | 11/2000 |
| WO | WO 01/00156 A1 | 1/2001 |
| WO | WO 01/00157 A1 | 1/2001 |
| WO | WO 01/17564 A2 | 3/2001 |
| WO | WO 01/17565 A2 | 3/2001 |
| WO | 02/087517 | 11/2002 |

* cited by examiner

SKIN CARE COMPOSITIONS ON A THIN SANITARY NAPKIN

CROSS REFERENCE TO RELATED APPLICATION

This application is a continuation-in-part of U.S. Ser. No. 10/152,924 filed on May 21, 2002 now abandoned, which is a continuation-in-part of U.S. Ser. No. 09/968,154 filed on Oct. 1, 2001 now abandoned. This application is also a continuation in part of U.S. Ser. No. 60/581,483, filed Jun. 21, 2004.

FIELD OF INVENTION

The present invention relates to skin care compositions which are effective in the control of skin disorders such as skin erythema, malodor, and skin bacterial infections. In particular, the present invention relates to skin care compositions, and thin absorbent articles containing the skin care compositions.

BACKGROUND OF THE INVENTION

Antimicrobial agents are commonly used in the treatment of skin abnormalities or disorders that can lead to acute or chronic symptoms such as redness, acne, inflammation, rash, burning, stinging, itching, flaking/scaling skin, malodor, and the like. The antimicrobial agent can provide a dermatological, and/or therapeutic effect in the treatment of the skin abnormalities or disorders. Therefore, antimicrobial agents are also commonly referred to as "antimicrobes", "active agents", "antibacterial agents", "bacteriocides", "enzyme inhibitors", "anti-acne agents", "antifingal agents", "antiviral agents", and so forth.

The type of antimicrobial agent used to treat the skin disorder will generally depend upon the acute or chronic symptom. For example, lipase and/or protease inhibitors are typically used to treat diaper rash, salicylic acid and N-acetyl-L-cysteine compounds are typically used to treat acne, and hexamidine and pentamidine compounds are typically used to prevent the formation and growth of bacteria and fungi. These antimicrobial agents can be used alone or in combination with other antimicrobes at reported individual concentrations of at least about 1% to provide a skin treatment benefit.

One reported attempt of using an antimicrobial agent such as hexamidine to treat fecal proteases is disclosed in WO 99/45974. This reference discloses the application of a protease inhibitor such as hexamidine onto an absorbent article for ultimate delivery of the hexamidine onto the skin, resulting in the transfer of a protease inhibitor having defined assay parameters such as an $IC_{50}$ of 30 μM or less. The hexamidine protease inhibitor, particularly hexamidine diisethionate, described in the WO 99/45974 reference is typically employed at concentrations of about 1% or greater.

Another reported attempt of using one or more antimicrobial agents to prevent or treat skin disorders such as diaper dermatitis is disclosed in WO/45973. WO/45973 discloses skin care compositions comprising compounds such as hexamidine and its salts that can be included in the skin care compositions with other known skin active agents such as panthenol, and zinc oxide applied to absorbent articles. The WO/45973 reference also discloses the employment of hexamidine antimicrobial agents at effective concentrations of about 10%.

It has been found, however, that hexamidine can be included in skin care compositions at low concentrations (about 0.1% or less) to provide effective skin treatment benefits such as the prevention and reduction of erythema, malodor, and other bacterial skin disorders when used in combination with a low concentration of other skin active agents such as zinc oxide and/or niacinamide.

SUMMARY OF THE INVENTION

Disclosed is a sanitary napkin for wearing adjacent the pudendal region, the sanitary napkin having a skin care composition applied thereon, wherein the sanitary napkin has a caliper less than about 5.0 mm. The skin care composition can be hydrophilic or hydrophobic, and can have from about 0.001% to about 0.1% by weight of hexamidine, from about 0.001% to about 10% by weight of zinc oxide, from about 0.01% to about 10% by weight of niacinamide, and a carrier.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

DETAILED DESCRIPTION OF THE DRAWINGS

Figure 1:
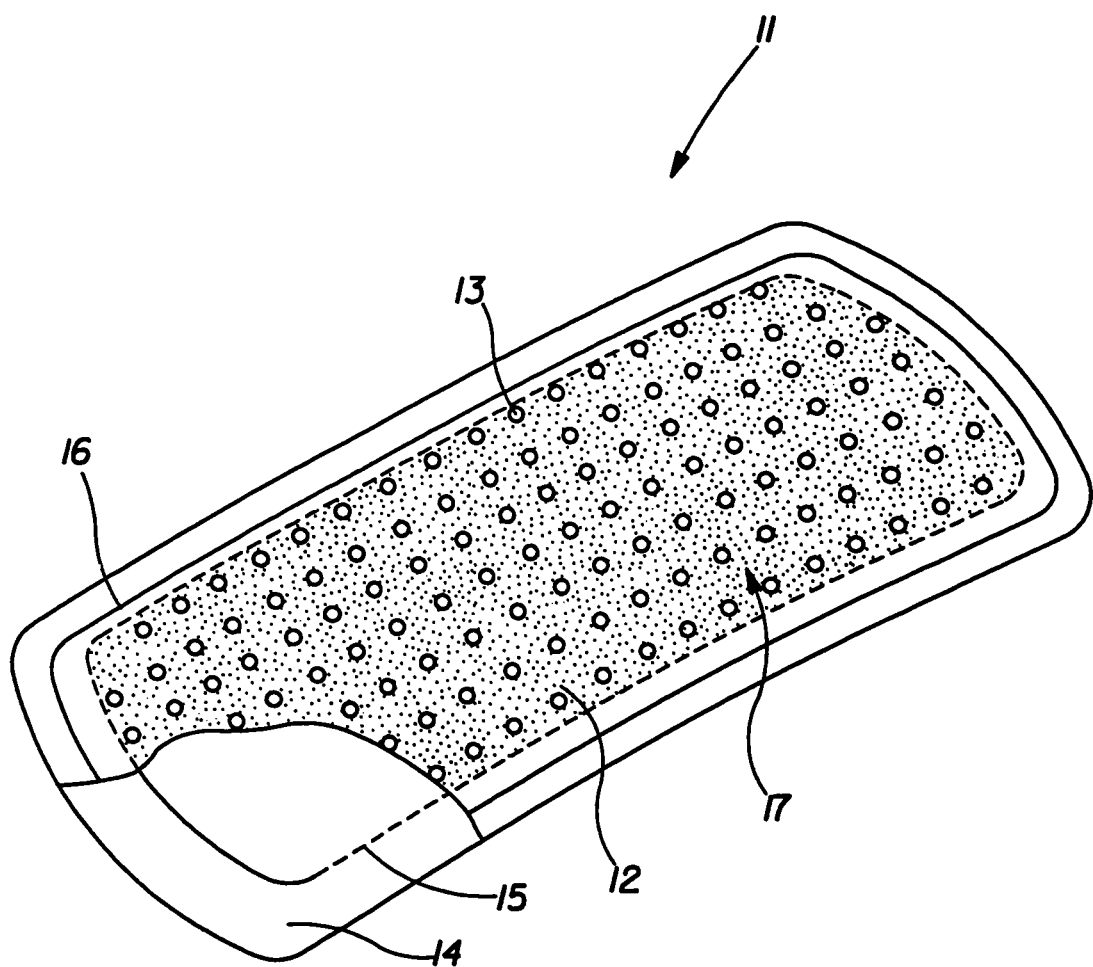
FIGS. 1-2 are views of an apertured panty liner and an interlabial product respectively. Both contain a skin care composition.

FIG. 1 shows an apertured panty liner 11 comprising a topsheet 12 containing apertures 13, a liquid impervious backsheet 14 bonded to the topsheet 12 along a sealing line 16, and an absorbent core 15. The topsheet 12 also contains a skin care composition 17 disposed on its top surface, wherein the skin care composition 17 is distributed onto the topsheet 12 such that it remains on the top surface and not within the apertures 13 for effective transfer of the skin care composition 17 onto the skin of a wearer.

Figure 2:
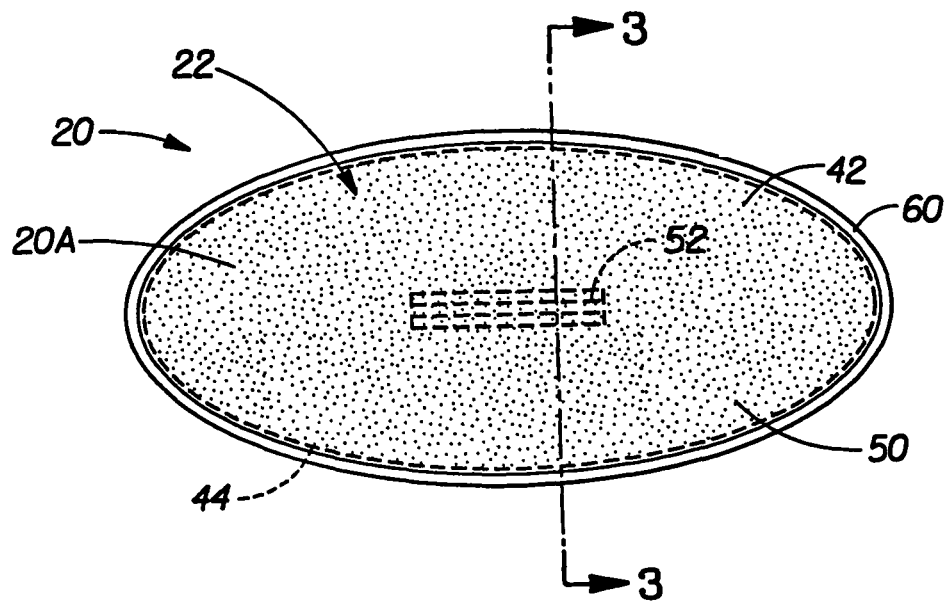
Figure 3:
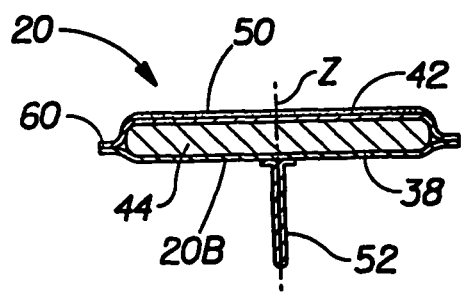
FIG. 3 is a cross sectional view of the absorbent interlabial product shown in FIG. 2, taken along line 3-3.

FIG. 2 shows an interlabial product containing a skin care composition. FIG. 3 is a cross sectional view of the interlabial product shown in FIG. 3, taken along line 4-4 of FIG. 2. The interlabial product 20 as shown in FIGS. 2-3 has a body-contacting side 20A and a garment surface 20B. The interlabial product comprises a pad-like main body portion 22 and an optional placement and removal tab 52 which is joined to the underside 20B of the main body portion 22 to provide the overall interlabial product with a "T"-shaped cross-sectional configuration. As shown in FIGS. 2-3 the main body portion 22 comprises a topsheet 42, a liquid impervious backsheet 38 joined to the topsheet 42 along a seam 60, and an absorbent core 44. The skin care composition 50 is disposed on the topsheet 42. The interlabial product 20 is also suitable for use as a hemorrhoid patch.

Figure 4:
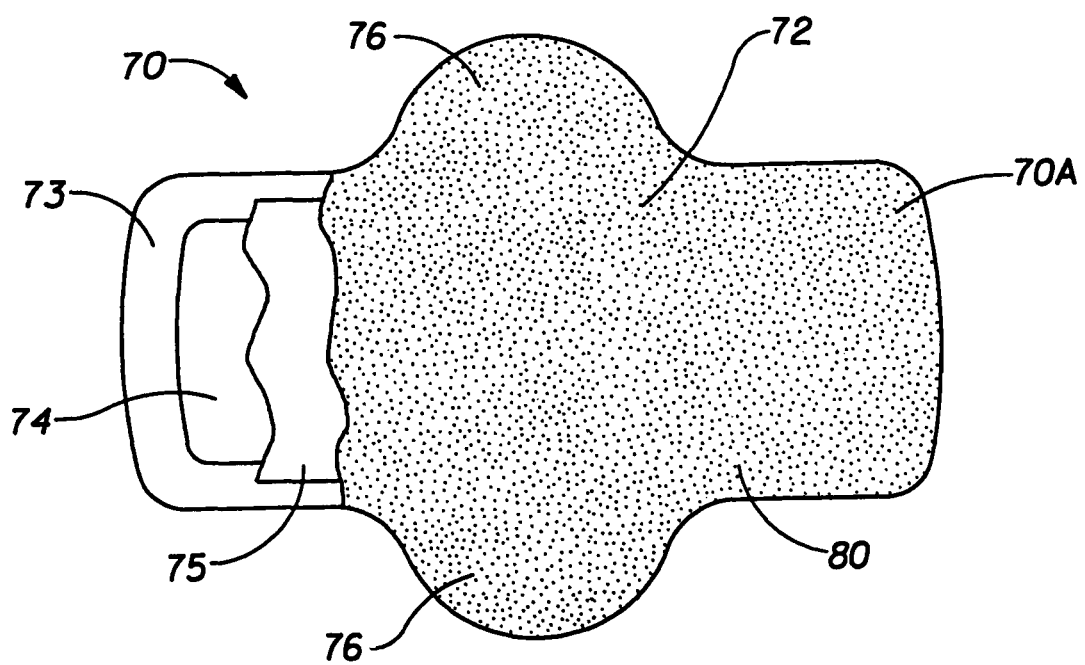
FIG. 4 is a view of a sanitary napkin containing a skin care composition.

FIG. 4 shows a sanitary napkin 70 having a body-contacting surface 70A comprising a topsheet 72, a liquid impervious backsheet 73 joined to the topsheet 72, an absorbent core 74, and a fluid acquisition layer 75 to promote fluid transport to the absorbent core 74. The sanitary napkin 70 may also be provided with additional features commonly found in napkins, including "wings" or "flaps" such as wings 76. The topsheet 72 portion of the sanitary napkin 70 has a skin care composition 80 disposed onto the topsheet.

Figure 5:
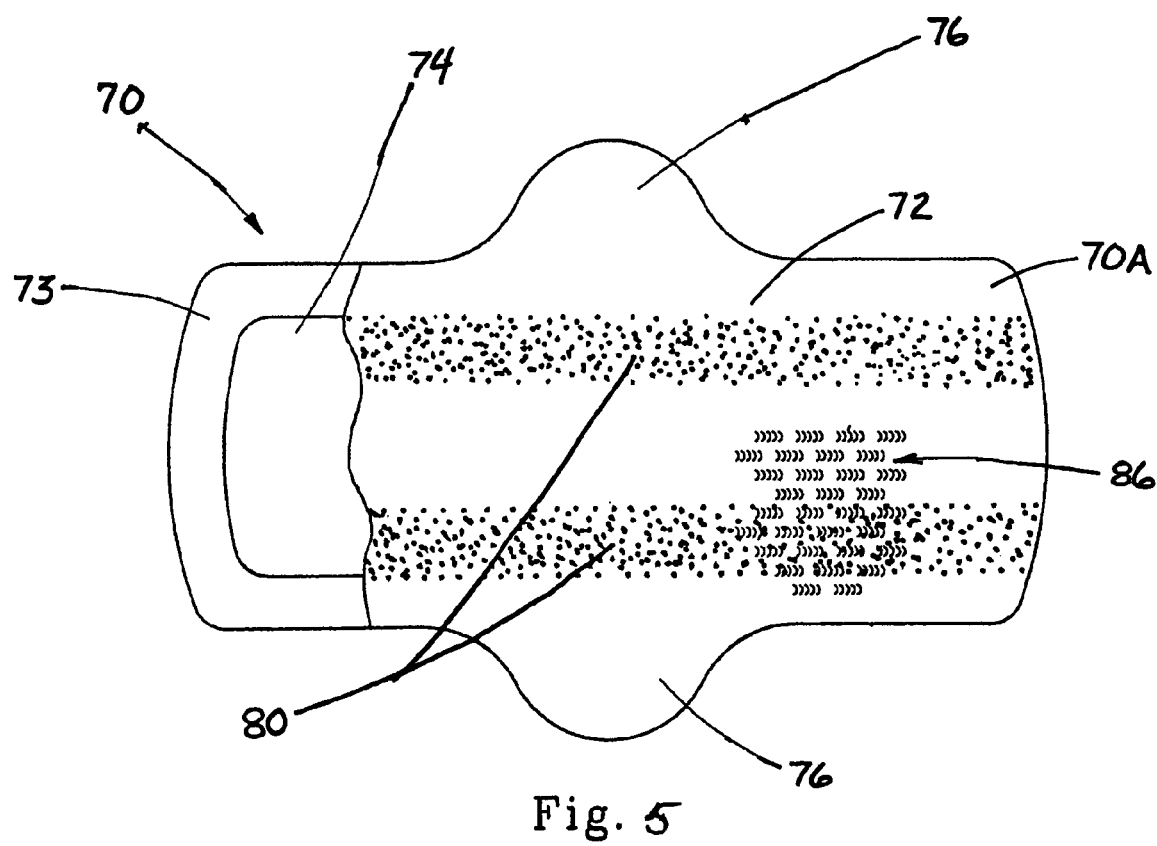
FIG. 5 is a view of a sanitary napkin containing a skin care composition.

FIG. 5 shows a sanitary napkin 70 having a body-contacting surface 70A, a topsheet 72, a liquid impervious backsheet 73 joined to the topsheet 72, an absorbent core 74, and wings 76. The topsheet 72 comprises tufts 86, and a skin care composition 80 disposed in stripes onto the topsheet.

DETAILED DESCRIPTION OF THE INVENTION

The skin care compositions of the present invention comprise a select combination of skin treatment agents such as hexamidine, zinc oxide, and niacinamide which are highly effective in the prevention and treatment of erythema, malodor, and bacterial skin disorders, especially when these skin care compositions are administered to the skin from application on absorbent articles.

The term "absorbent article" as used herein refers to devices which are placed against or in close proximity to the body of the wearer to absorb and contain various exudates discharged from the body. Examples of such absorbent articles include panty liners, diapers, training pants, catamenials, sanitary pads, bandages, incontinence briefs, interlabials, hemorrhoid patches, and the like. Likewise, the term "disposable absorbent article" as used herein refers to devices which absorb and contain body exudates, and which are not intended to be laundered or otherwise restored or reused as an absorbent article. The disposable absorbent articles for use herein are intended to be discarded after a single use, and preferably, to be recycled, composted, or otherwise disposed of in an environmentally compatible manner. The term "skin treatment agent" as used herein refers to materials that when applied topically and internally to the skin are capable of preventing, reducing, and/or eliminating any occurrence of skin disorders, particularly skin disorders associated with erythema, malodor, and bacterial infections. The term "skin disorders" as used herein refers to symptoms associated with irritating, acute, or chronic skin abnormalities. Examples of such symptoms include, but are not limited to, itching, inflammation, rash, burning, stinging, redness, swelling, sensitivity, sensation of heat, flaking/scaling, malodor, and the like. The term "ambient conditions" as used herein refers to surrounding conditions at about one atmosphere of pressure, at about 50% relative humidity, and at about 25° C.

The skin care compositions of the present invention can comprise, consist of, or consist essentially of the elements and limitations of the invention described herein, as well as any of the additional or optional ingredients, components, or limitations described herein. All percentages, parts and ratios are by weight of the total composition, unless otherwise specified. All such weights as they pertain to listed ingredients are based on the specific ingredient level and, therefore, do not include carriers or by-products that may be included in commercially available materials, unless otherwise specified.

I. Skin Treatment Agents

The skin care compositions of the present invention comprise relatively low concentrations of a select combination of skin treatment agents that are capable of reducing and eliminating the occurrence of skin disorders that can result from contact between the skin and moisture-laden air, skin disorders resulting from prolonged moist human tissue that can occur from the skin being exposed to moisture or other body exudates, and/or skin disorders that are generated from contact between the skin and microbial or bacterial agents. The phrase "select combination of skin treatment agents" refers to the following combinations: a. hexamidine, zinc oxide, and niacinamide; b. hexamadine and zinc oxide; and c. hexamadine and niacinamide.

Surprisingly, the select combination of skin treatment agents can be included at low individual concentrations, relative to their use in the prior art, and still be effective. For example, the skin care compositions of the present invention can include hexamidine at a concentration of about 0.1% or less by weight, zinc oxide at a concentration of about 1% or less by weight, and niacinamide at a concentration of about 2% or less by weight to achieve equal or superior benefits in the prevention and/or treatment of skin disorders as compared to known skin care compositions that generally comprise these skin treatment agents at higher levels. Similarly, the total effective concentration of the select combination of skin treatment agents in the compositions of the present invention are also relatively low. The total concentration of the select combination of skin treatment agents ranges from about 0.002% to about 10%, preferably from about 0.01% to about 5%, more preferably from about 0.1% to about 2% by weight of the skin care composition.

A. Hexamidine:

The skin care compositions of the present invention comprise hexamidine skin treatment agent at concentrations ranging from about 0.001% to about 0.1%, from about 0.005% to about 0.1%, or even from about 0.01% to about 0.1% by weight of the composition. The hexamidine skin treatment agent suitable for use herein include those aromatic diamines which generally conform to the following formula:

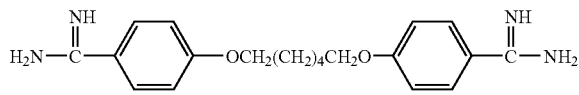

These aromatic diamines are referred to as 4,4'-[1,6-Hexanediylbis(oxy)]bisbenzenecarboximidamide; 4,4'-(hexamethylenedioxy)dibenzamidine; and 4,4'-diamidino-α,ω-diphenoxyhexane. The most popular employed form of hexamidine is the general category of hexmidine salts, which include acetate, salicylate, lactate, gluconate, tartarate, citrate, phosphate, borate, nitrate, sulfate, and hydrochloride salts of hexamidine. Specific nonlimiting examples of hexamidine salts include hexamidine isethionate, hexamidine diisethionate, hexamidine hydrochloride, hexamidine gluconate, and mixtures thereof. Hexamidine isethionate and hexamidine diisethionate are β-hydroxyethane sulfonate salts of hexamidine which are preferred for use herein as a skin treatment agent in the prevention and/or treatment of skin disorders. Hexamidine diisethionate is the most preferred hexamidine compound suitable for use as the skin treatment agent herein and is available from Laboratories Serolobilogiques (Pulnoy, France) and the Cognis Incorporation (Cincinnati, Ohio) under the tradename ELASTAB HP100.

Hexamidine compounds are known as effective skin treatment agents that can control microbial growth that can lead to irritating and itching skin disorders. Therefore, these skin treatment agents are often referred to as antimicrobial agents. As used herein the term "antimicrobial agents" refer to materials which function to destroy or suppress the growth or metabolism of microbes, and include the general classification of antibacterial, antifungal, antiprotozoal, antiparasitic, and antiviral agents.

It has been found, however, that a low concentration (about 0.1% or less by weight) of hexamidine provides for improved reduction and/or prevention of skin irritating infections, especially when a low amount of hexamidine is combined with a low concentration of other antimicrobial agents such as zinc oxide and/or niacinamide. This combination of hexamidine and zinc oxide and/or niacinamide can be administered topically and internally at a total concentration less than an effective amount of an applied dosage of these individual compounds. As used herein the term "effective amount" refers to an amount with provides a therapeutic benefit with minimal or no adverse reaction in the reduction and/or prevention of any noticeable or unacceptable skin abnormality which causes irritating, acute, or chronic symptoms including itching and inflammation.

Other aromatic diamines are also suitable for use as a skin treatment agent herein. Such compounds include butamidine and derivatives thereof including butamidine isethionate; pentamidine and derivatives thereof including pentamidine isethionate and pentamidine hydrochloride; dibromopropamidine and derivatives thereof including dibromopropamidine isethionate; stilbamidine and derivatives thereof including hydroxystilbamidine, stilbamidine dihydrochloride, and stilbamidine isethionate; diaminodiamidines and derivatives thereof; and mixtures thereof.

B. Zinc Oxide:

The skin care compositions of the present invention comprise zinc oxide skin treatment agent at concentrations ranging from about 0.001% to about 10%, preferably from about 0.005% to about 5%, more preferably from about 0.005% to about 2%, most preferably from about 0.01% to about 1% by weight of the composition. The zinc oxide skin treatment agent can be included in the compositions as an individual zinc oxide compound or a combination of zinc oxides, provided that the individual or combined zinc oxide can readily combine with the hexamidine and niacinamide skin treatment agents to provide antimicrobial benefits.

The zinc oxide skin treatment agent suitable for use herein include those inorganic white and yellowish-white powders that conform to the formula ZnO, and that are more fully described in *The Merck Index*, Eleventh Edition, entry 10050, p. 1599 (1989). Some particularly useful forms of zinc oxide include those that are manufactured and commercially available in average particle size diameters that range from about 1 nm (nanometer) to about 10 μm (micrometer), alternatively from about 10 nm to about 1 μm or even from about 20 nm to about 500 nm. Surprisingly, the inventors have discovered that the use of the above mentioned, relatively small nanoparticle diameter size zinc oxide avoids undesirable skin or hair whitening that results from the transfer of the zinc oxide containing emollient from the topsheet of absorbent article to the wearer's body during product use. This is a particular benefit when the product is a panty liner, sanitary napkin, incontinence brief, or other absorbent article intended to be used by adults having hair in the region where the skin care composition will transfer.

Commercially available zinc oxides include the white zinc oxide powders sold under the tradename ULTRAFINE 350 which is commercially available from the Kobo Incorporation located in South Plainfield, N.J. Other suitable zinc oxide materials include a premix of zinc oxide and a dispersing agent such as polyhydroxystearic acid wherein this premix is available from the Uniqema Incorporation (Wilmington, Del.) under the tradename Arlecel® P100; and a premix of zinc oxide and an isononyl isononanoate dispersing agent which is available from the Ikeda Incorporation (Island Park, N.Y.) under the tradename Salacos® 99.

C. Niacinamide:

The skin care compositions of the present invention comprise niacinamide skin treatment agent as an individual niacinamide or as a combination of niacinamides at a total niacinamide concentration ranging from about 0.01% to about 10%, preferably from about 0.05% to about 5%, more preferably from about 0.2% to about 2% by weight of the skin care composition. The niacinamide skin treatment agent provides for skin conditioning benefits as well as providing for increased efficacy of the skin treatment agents in controlling skin disorders.

Nonlimiting examples of niacinamide skin treatment agents suitable for use in the skin care compositions of the present invention include those niacinamide compounds that are amide derivatives of nicotinic acid, and that generally conform to the following formula:

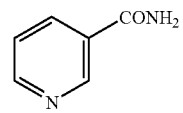

Niacinamide and nicotinic acid are also known as Vitamin $B_3$ and Vitamin $B_5$, whereas niacinamide is the commonly used active form. Niacinamide derivatives including salt derivatives are also suitable for use herein as a skin treatment agent. Nonlimiting specific examples of suitable niacinamide derivatives include nicotinuric acid and nicotinyl hydroxamic acid.

The niacinamide skin treatment agent can also be included in the composition as acidified niacinamide compounds. The process of acidifying niacinamide compounds is within the gambit of those skilled in the art, wherein one such technique involves dissolving niacinamide in an alcohol solution, adding while stirring an equal molar amount of a fatty acid such as stearic acid (e.g., mixing 1 part niacinamide to 2.4 parts stearic acid), and then air drying the mixture until the alcohol evaporates. A suitable stearic acid compound that can be used in the process of acidifying niacinamide is stearic acid sold under the tradename Emersol® 150 which is available from the Cognis Corporation.

Examples of the above niacinamide compounds are well known in the art and are commercially available from a number of sources, for example, the Sigma Chemical Company (St Louis, Mo.); ICN Biomedicals, Incorporation (Irvin, Calif.); Aldrich Chemical Company (Milwaukee, Wis.); and Em Industries HHN (Hawthorne, N.Y.).

D. Optional Components:

Nonlimiting examples of optional suitable skin treatment actives useful in the present invention include allantoin; aluminum hydroxide gel; calamine; cysteine hydrochloride; racemic methionine; sodium bicarbonate; Vitamin C and derivatives thereof; protease inhibitors including serine proteases, metalloproteases, cysteine proteases, aspartyl proteases, peptidases, and phenylsulfonyl fluorides; lipases; esterases including diesterases; ureases; amylases; elastases; nucleases; guanidinobenzoic acid and its salts and derivatives; herbal extracts including chamomile; and mixtures thereof. Guanidinobenzoic acid and its salts and derivatives are more fully described in U.S. Pat. No. 5,376,655, issued to Imaki et al. on Dec. 27, 1994. These other suitable skin treatment actives are typically included at concentrations ranging from about 0.001% to about 10% by weight of the skin care composition.

Furthermore, one or more optional components known or otherwise effective for use in skin care compositions may be included provided that the optional components are physically and chemically compatible with the essential skin treatment and carrier components, or do not otherwise unduly impair product stability, aesthetics, or performance. Such optional components are typically included at concentrations ranging from about 0.001% to about 20% by weight of the compositions, and include materials such as water, skin conditioning agents, perfumes, deodorants, opacifiers, astringents, preservatives, emulsifying agents, film formers, stabilizers, proteins, lecithin, urea, colloidal oatmeal, pH control agents, and other Monographed materials that are deemed safe by the U.S. Food and Drug Administration (FDA) under 21 C.F.R. §347 for use on human skin. Other optional components for use in the skin care compositions of the present invention include fats or oils, or essential oils. These oils can be present at concentrations ranging from about 0.0001% to 10% by weight of the compositions, and include materials such as Anise Oil, Balm Mint Oil, Bee Balm Oil, Birch Oil, Bitter Almond Oil, Bitter Orange Oil, Calendula Oil, California Nutmeg Oil, Caraway Oil, Chamomile Oil, Cinnamon Oil, Cloveleaf Oil, Clove Oil, Coriander Oil, Cypress Oil, Eucalyptus Oil, Fennel Oil, Gardenia Oil, Geranium Oil, Ginger Oil, Grapefruit Oil, Hyptis Oil, Juniper Oil, Kiwi Oil, Laurel Oil, Lavender Oil, Lemongrass Oil, Lemon Oil, Lovage Oil, Mandarin Orange Oil, Musk Rose Oil, Nutmeg Oil, Olibanum, Orange Flower Oil, Orange Oil, Peppermint Oil, Pine Oil, Rose Hips Oil, Rosemary Oil, Rose Oil, Rue Oil, Sage Oil, Sandalwood Oil, Sassafras Oil, Spearmint Oil, Sweet Maijoram Oil, Sweet Violet Oil, Tea Tree Oil, Thyme Oil, Wild Mint Oil, Yarrow Oil, Ylang Ylang Oil, Apricot Kernel Oil, Avocado Oil, Babassu Oil, Borage Seed Oil, Butter, C12-C1. Acid Triglyceride, Camellia Oil, Canola Oil, Caprylic/Capric/Lauric Triglyceride, Caprylic/Capric/Linoleic Triglyceride, Caprylic/Capric/Stearic Triglyceride, Caprylic/Capric305 Triglyceride, Carrot Oil, Cashew Nut Oil, Castor Oil, Cherry Pit Oil, Cocoa Butter, Coconut Oil, Cod Liver Oil, Corn Germ Oil, Corn Oil, Cottonseed Oil, C10-C1 Triglycerides, Evening Primrose Oil, Glyceryl Triacetyl Hydroxystearate, Glyceryl Triacetyl Ricinoleate, Glycosphingolipids, Grape Seed Oil, Hazelnut Oil, Human Placental Lipids, Hybrid Safflower Oil, Hybrid Sunflower Seed Oil, Hydrogenated Castor Oil, Hydrogenated Coconut Oil, Hydrogenated Cottonseed Oil, Hydrogenated C2-C1 Triglycerides, Hydrogenated Fish Oil, Hydrogenated Lard, Hydrogenated Menhaden Oil, Hydrogenated Mink Oil, Hydrogenated Orange Roughy Oil, Hydrogenated Palm Kernel Oil, Hydrogenated Palm Oil, Hydrogenated Peanut Oil, Hydrogenated Shark Liver Oil, Hydrogenated Soybean Oil, Hydrogenated Tallow, 315 Hydrogenated Vegetable Oil, Lard, Lauric/Palmitic/Oleic Triglyceride, Lanolin and Lanolin derivatives, Lesquerella Oil, Macadamia Nut Oil, Maleated Soybean Oil, Meadowfoam Seed Oil, Menhaden Oil, Mink Oil, Moringa Oil, Mortierella Oil, Oleic/Linoleic Triglyceride, Oleic/Paimitic/Lauric/Myristic/Linoleic Triglyceride, Oleostearine, Olive Husk Oil, Olive Oil, Ornental Lipids, Palm Kernel Oil, Palm Oil, 320 Peach Kernel Oil, Peanut Oil, Pentadesma Butter, Phospholipids, Pistachio Nut Oil, Rapeseed Oil, Rice Bran Oil, Safflower Oil, Sesame Oil, Shark Liver Oil, Shea Butter, Soybean Oil, Sphingolipids, Sunflower Seed Oil, Sweet Almond Oil, Tall Oil, Tallow, Tribehenin, Tricaprin, Tricaprylin, Triheptanoin, C10 Fatty Acids: Arachidic Acid, Behenic Acid, Capric Acid, Caproic Acid, 330 Caprylic Acid, Coconut Acid, Corn Acid, Cottonseed Acid, Hydrogenated Coconut Acid, Hydrogenated Menhaden Acid, Hydrogenated Tallow Acid, Hydroxystearic Acid, Isostearic Acid, Lauric Acid, Linoleic Acid, Linolenic Acid, Myristic Acid, Oleic Acid, Palmitic Acid, Palm Kernel Acid, Pelargonic Acid, Ricinoleic Acid, Soy Acid, Stearic Acid, Tallow Acid, Undecanoic Acid, Undecylenic Acid, Wheat Germ Acid, and the like, as well as mixtures thereof. Specific optional skin care conditioning agents found useful in the present invention include panthenol, glycerine, and chamomile oil which are described in detail hereinbelow.

Panthenol:

Where included, panthenol typically comprises from about 0.001% to about 10%, preferably from about 0.005% to about 5%, more preferably from about 0.05% to about 1% by weight of the skin care composition. The optional panthenol skin conditioning agent provides for skin emolliency benefits that can leave the skin feeling smooth, soothing, and soft during and after interaction of the skin tissues with the skin treatment agents. The skin care compositions of the present invention can include an individual panthenol compound or a mixture of panthenol compounds.

Nonlimiting examples of panthenol include those panthenol compounds which are alcohol or ester derivatives of pantothenic acid. Pantothenic acid is a member of the B complex family and is often referred to as Vitamin $B_3$. Like pantothenic acid, the panthenol alcohol derivatives of this acid can exist as stereoisomers, for example, the D(+) form, the L(−) form, the racemate, and mixtures of the D(+) and L(−) forms. Specific examples of panthenol include, but are not limited to, D-panthenol (a.k.a. dexpanthenol), and dl-panthenol. Panthenol is more fully described in *The Merck Index*, Eleventh Edition, entry 2924, p. 464 (1989), which description is incorporated herein by reference. Examples of commercially available panthenol include D-panthenol which is available from Roche Vitamins Incorporation (Nutley, N.J.), a subsidiary of F. Hoffman LaRoche, Ltd.

Glycerine:

Where included, the skin care compositions comprise the preferred optional glycerine skin conditioning agent at concentrations ranging from about 0.01% to about 10%, preferably from about 0.02% to about 5%, more preferably from about 0.05% to about 2% by weight of the skin care composition. The optional glycerine skin conditioning agent also provides for skin emolliency benefits such as smooth, soothing, and soft feeling skin, as well as being a dispersing agent for the niacinamide skin treatment agent.

Glycerine is a C3 monohydric alcohol that is also referred to as glycerol and 1,2,3-propanetriol. Glycerine derivatives are also suitable for use as an optional skin conditioning agent herein wherein such derivatives include polyglycerols having from about 2 to about 16 repeating glycerol moieties. A specific example of a suitable glycerine skin conditioning agent is Glycerine, USP Kosher® which is commercially available from the Procter & Gamble Company located in Cincinnati, Ohio.

Chamomile:

The skin care compositions comprise the preferred optional chamomile oil at concentrations ranging from about 0.0001% to about 10%, preferably from about 0.001% to about 5%, more preferably from about 0.005% to about 2% by weight of the skin care composition. The optional chamomile oil skin conditioning agent also provides for skin benefits such as soothing. Chamomile oil is commonly prepared as an oil extract of chamomile flowers. An example of a commercially available chamomile oil include Phytoconcentrol Chamomile which is available from Dragoco Incorporation (Totowa, N.J.).

II. Carrier:

The skin care compositions of the present invention comprise a carrier for the skin treatment agents. The carrier can be included in the compositions as an individual carrier or a combination of carrier ingredients, provided that the total carrier concentration is sufficient to provide transfer and/or migration of the skin treatment agents onto the skin. The carrier can be a liquid, solid, or semisolid carrier material, or a combination of these materials, provided that the resultant carrier forms a homogenous mixture or solution at selected processing temperatures for the resultant carrier system and at processing temperatures for combining the carrier with the skin treatment agents in formulating the skin care compositions herein. Processing temperatures for the carrier system typically range from about 60° C. to about 90° C., more typically from about 70° C. to about 85° C., even more typically from about 70° C. to about 80° C.

The skin care compositions of the present invention typically comprise the carrier at a total carrier concentration ranging from about 60% to about 99.9%, preferably from about 70% to about 98%, more preferably from about 80% to about 97% by weight of the skin care composition. Suitable carrier compounds include petroleum-based hydrocarbons having from about 4 to about 32 carbon atoms, fatty alcohols having from about 12 to about 24 carbon atoms, polysiloxane compounds, fatty acid esters, alkyl ethoxylates, lower alcohols having from about 1 to about 6 carbon atoms, low molecular weight glycols and polyols, fatty alcohol ethers having from about 12 to about 28 carbon atoms in their fatty chain, lanolin and its derivatives, glyceride and its derivatives including acetoglycerides and ethoxylated glycerides of $C_{12}$-$C_{28}$ fatty acids, and mixtures thereof.

Nonlimiting examples of suitable petroleum-based hydrocarbons having from about 4 to about 32 carbon atoms include mineral oil, petrolatum, isoparaffins, various other branched chained hydrocarbons, and combinations thereof. Mineral oil is also known as "liquid petrolatum", and usually refers to less viscous mixtures of hydrocarbons having from about 16 to about 20 carbon atoms. Petrolatum is also known as "mineral wax", "petroleum jelly", and "mineral jelly", and usually refers to more viscous mixtures of hydrocarbons having from about 16 to about 32 carbon atoms. An example of commercially available petrolatum include petrolatum sold as Protopet® 1S which is available from the Witco Corporation located in Greenwich, Conn.

Nonlimiting examples of suitable fatty alcohols having from about 12 to about 24 carbon atoms include saturated, unsubstituted, monohydric alcohols or combinations thereof, which have a melting point less than about 110° C., preferably from about 45° C. to about 110° C. Specific examples of fatty alcohol carriers for use in the skin care compositions of the present invention include, but are not limited to, cetyl alcohol, stearyl alcohol, cetearyl alcohol, behenyl alcohol, arachidyl alcohol, lignocaryl alcohol, and combinations thereof. Examples of commercially available cetearyl alcohol is Stenol 1822 and behenyl alcohol is Lanette 22, both of which are available from the Cognis Corporation located in Cincinnati, Ohio.

Nonlimiting examples of suitable fatty acid esters include those fatty acid esters derived from a mixture of $C_{12}$-$C_{28}$ fatty acids and short chain ($C_1$-$C_8$, preferably $C_1$-$C_3$) monohydric alcohols preferably from a mixture of $C_{16}$-$C_{24}$ saturated fatty acids and short chain ($C_1$-$C_8$, preferably $C_1$-$C_3$) monohydric alcohols. Representative examples of such esters include methyl palmitate, methyl stearate, isopropyl laurate, isopropyl myristate, isopropyl palmitate, ethylhexyl palmitate, and mixtures thereof. Suitable fatty acid esters can also be derived from esters of longer chain fatty alcohols ($C_{12}$-$C_{28}$, preferably $C_{12}$-$C_{16}$) and shorter chain fatty acids such as lactic acid, specific examples of which include lauryl lactate and cetyl lactate.

Nonlimiting examples of suitable alkyl ethoxylates include $C_{12}$-$C_{22}$ fatty alcohol ethoxylates having an average degree of ethoxylation of from about 2 to about 30. Nonlimiting examples of suitable lower alcohols having from about 1 to about 6 carbon atoms include ethanol, isopropanol, butanediol, 1,2,4-butanetriol, 1,2 hexanediol, ether propanol, and mixtures thereof. Nonlimiting examples of suitable low molecular weight glycols and polyols include ethylene glycol, polyethylene glycol (e.g., Molecular Weight 200-600 g/mole), butylene glycol, propylene glycol, polypropylene glycol (e.g., Molecular Weight 425-2025 g/mole), and mixtures thereof. A more detailed description of carrier ingredients including suitable hydrocarbons, polysiloxane compounds, and fatty alcohol ethoxylates can be found in U.S. Pat. No. 5,643,588, issued Jul. 1, 1997 to Roe et al. entitled "Diaper Having A Lotioned Topsheet".

In one embodiment, the carrier comprises a combination of one or more petroleum-based hydrocarbons and one or more fatty alcohols described hereinabove. When one or more petroleum-based hydrocarbons having from about 4 to about 32 carbon atoms are used in combination with one or more fatty alcohols having from about 12 to about 22 carbon atoms, the petroleum-based hydrocarbons are included at total concentrations ranging from about 20% to about 99%, preferably from about 30% to about 85%, more preferably from about 40% to about 80% by weight of the skin care composition; wherein the fatty alcohols are included at total concentrations ranging from about 0.2% to about 65%, preferably from about 1% to about 50%, more preferably from about 2% to about 40% by weight of the skin care composition.

It is believed that a petroleum-based carrier system comprising $C_4$-$C_{32}$ hydrocarbons, $C_{12}$-$C_{22}$ fatty alcohols, and fumed silica provides a homogeneous mixture of the carrier, skin treatment agents, and any optional ingredients wherein this homogeneous mixture ensures sufficient contact between the skin and skin treatment agents to result in effective prevention and treatment of skin disorders. The fumed silica suitable for inclusion in the preferred petroleum-based carrier system, or with any other carrier described herein, includes colloidal pyrogenic silica pigments which are sold under the Cab-O-Sil® tradename, and which are commercially available from the Cabot Corporation located in Tuscola, Ill. These colloidal pyrogenic silica pigments are submicroscopic particulated pyrogenic silica pigments having mean particle sizes ranging from about 0.1 microns to about 100 microns. Specific examples of commercially available Cab-O-Sil® silica pigments include Cab-O-Sil® TS-720 (a polydimethylsiloxane treated fumed silica), Cab-O-Sil® TS-530 (a trimethyl silanized fumed silica), and Cab-O-Sil® TS-610 (a dimethyldisilanized fumed silica). The fumed silica provides the skin care compositions with desired viscosity or thickening properties, and is typically included at concentrations ranging from about 0.01% to about 15%, preferably from about 0.1% to about 10%, more preferably from about 1% to about 5% by weight of the skin care composition.

The fumed silica can be used alone or in combination with other optional viscosity or thickening agents such as talc, bentonites including treated bentonites, hectorites including treated hectorites, calcium silicates including treated calcium silicates, magnesium silicates, magnesium aluminum silicates, zinc stearates, sorbitol, colloidal silicone dioxides, spermaceti, carnuba wax, beeswax, candelilla wax, paraffin wax, microcrystalline wax, castrol wax, ceresin, esparto, ouricuri, rezowax, polyethylene wax, $C_{12}$-$C_{24}$ fatty acids, polyhydroxy fatty acid esters, polyhydroxy fatty acid amides, polymethacrylate polymers, polymethacrylate and styrene copolymers, and combinations thereof. These other optional viscosity modifying or thickening agents are also included at total concentrations ranging from about 0.01% to about 15% by weight of the skin care composition. A nonlimiting specific example of another suitable viscosity or thickening agent include bentonite sold as Bentone® 38 which is available from the Rheox Incorporation.

III. Absorbent Article

The skin care compositions of the present invention are preferably administered to the skin from application of the compositions onto a disposable absorbent article. These products may comprise a topsheet, a backsheet, and an absorbent core positioned between the topsheet and backsheet; each component having a body- or wearer-contacting surface and a garment surface. The terms "body-contacting surface" and "wearer-contacting surface" are used interchangeably herein and refer to one or more surfaces of any article component that is intended to be worn or positioned toward or adjacent the body of the wearer/user for contact between the wearer/user and the article's surface at some time during the use period. The term "garment surface" as used herein refers to the outer or exterior surface of any article component that is intended to be worn or positioned adjacent a wearer's undergarments, or in the case of an absorbent article which is not worn by the user, the garment surface is typically positioned adjacent a user's hand or other implement assisting in the use of the absorbent article. As used herein, the term "wearer" and "user" are used interchangeably as the present invention contemplates absorbent articles which may not be intended to be worn, but rather used to absorb bodily exudates while transferring the skin care compositions of the present invention. For instance, bandages (which may not comprise a backsheet) are also contemplated absorbent articles of the present invention.

The absorbent articles described herein may further comprise one or more optional components such as fastening devices such as adhesives, tapes, and VELCRO systems; waistbands including elastic and extensible waistbands; waistbelts; elastic leg cuffs; extensible side panels; wings; additional fluid pervious or absorbent layers including fluid acquisition layers, fluid distribution layers, fluid storage layers and combinations of these layers.

A. Topsheet:

The absorbent article may comprise any known or otherwise effective topsheet, such as one which is compliant, soft feeling, and non-irritating to the wearer's skin. Suitable topsheet materials include a liquid pervious material that is oriented towards and contacts the body of the wearer permitting bodily discharges to rapidly penetrate through it without allowing fluid to flow back through the topsheet to the skin of the wearer. The topsheet, while being capable of allowing rapid transfer of fluid through it, also provides for the transfer or migration of the skin care composition onto an external or internal portion of a wearer's skin. A suitable topsheet can be made of various materials such as woven and nonwoven materials; apertured film materials including apertured formed thermoplastic films, apertured plastic films, and fiber-entangled apertured films; hydro-formed thermoplastic films; porous foams; reticulated foams; reticulated thermoplastic films; thermoplastic scrims; or combinations thereof.

Apertured film materials suitable for use as the topsheet include those apertured plastic films that are non-absorbent and pervious to body exudates and provide for minimal or no flow back of fluids through the topsheet. Nonlimiting examples of other suitable formed films, including apertured and non-apertured formed films, are more fully described in U.S. Pat. No. 3,929,135, issued to Thompson on Dec. 30, 1975; U.S. Pat. No. 4,324,246, issued to Mullane et al. on Apr. 13, 1982; U.S. Pat. No. 4,324,314, issued to Radel et al. on Aug. 3, 1982; U.S. Pat. No. 4,463,045, issued to Ahr et al. on Jul. 31, 1984; U.S. Pat. No. 5,006,394, issued to Baird on Apr. 9, 1991; U.S. Pat. No. 4,609,518, issued to Curro et al. on Sep. 2, 1986; and U.S. Pat. No. 4,629,643, issued to Curro et al. on Dec. 16, 1986. Commercially available formed filmed topsheets include those topsheet materials marketed by the Procter&Gamble Company (Cincinnati, Ohio) under the DRI-WEAVE® tradename.

Nonlimiting examples of woven and nonwoven materials suitable for use as the topsheet include fibrous materials made from natural fibers, modified natural fibers, synthetic fibers, or combinations thereof. These fibrous materials can be either hydrophilic or hydrophobic. Alternatively, the topsheet can be rendered hydrophilic, in order to improve liquid transport through the topsheet, by the use of any known method for making topsheets containing hydrophilic components. One such method include treating an apertured film component of a nonwoven/apertured thermoplastic formed film topsheet with a surfactant as described in U.S. Pat. No. 4,950,264, issued to Osborn on Aug. 21, 1990. Osborn '264 (the disclosure of which is incorporated by reference herein below) describes a thin and flexible sanitary napkin for wearing adjacent to the pudendal region (i.e., the externally visible female genitalia) and having a caliper of about 4.0 mm to about 5.0 mm, but preferably less than about 3.0 mm, or less than about 2.6 mm, or less than about 2.2 mm, or less than about 2.0 mm. In one embodiment, the caliper is 1.9 mm. Osborn discloses a method of measuring caliper which includes the use of a comparator gauge, using a circular foot made of aluminium and having a weight of 10.0 grams and a contact surface of 5.16 square cm. Osborn discloses Other suitable methods describing a process for treating the topsheet with a surfactant are disclosed in U.S. Pat. Nos. 4,988,344 and 4,988,345, both issued to Reising et al. on Jan. 29, 1991. The topsheet can comprise hydrophilic fibers, hydrophobic fibers, or combinations thereof.

Examples of suitable natural woven and nonwoven fibrous materials include, but are not limited to, wood pulp fibers, cotton, hemp, wool, jute, silk, ramie, bagasse, Esparto grass, flax fibers, and mixtures thereof. Examples of suitable modified natural woven and nonwoven fibrous materials include chemically modified wood pulp fibers, ethyl cellulose fibers, cellulose acetates, cellulose esters, rayons, viscose fibers, and mixtures thereof. Examples of suitable synthetic woven and nonwoven fibrous materials include, but are not limited to, polyester fibers including polyethylene terephthalates, polypropylene fibers, polyethylene fibers, polysaccharide fibers, polyvinyl alcohol fibers, polyvinyl flouride fibers, polyvinyl chloride fibers, polyvinylidene chloride fibers, polyvinyl acetate fibers, polyethylvinyl acetate fibers, polytetrafluoroethylene fibers, starch base resins, polyurethanes, polystyrenes, polyamides including nylons, acrylics, and mixtures thereof.

When the topsheet comprises a nonwoven fibrous material in the form of a nonwoven web, the nonwoven web may be produced by any known procedure for making nonwoven webs, nonlimiting examples of which include spunbonding, carding, wet-laid, air-laid, meltblown, needle-punching, mechanical entangling, thermo-mechanical entangling, and hydroentangling. A specific example of a suitable meltblown process is disclosed in U.S. Pat. No. 3,978,185, to Buntin et al., issued Aug. 31, 1976.

Examples of suitable commercial nonwoven materials include nonwoven fabrics manufactured by the Fiber-web Group of Simpsonville, S.C. under the tradenames CELESTRA and HOLMESTRA; a nonwoven nylon co-polymer commercially available from Allied Signal Incorporation under the tradename Hydrofil SCFX; a nonwoven polyethylene fibrous material commercially available from the Dow Chemical Company under the tradename ASPUN; and nonwoven polypropylene fibrous materials commercially available from the Exxon Corporation under the tradenames ESCORENE 3,400 and ESCORENE 3,500.

Other suitable nonwoven materials include low basis weight nonwovens, that is, nonwovens having a basis weight of from about 18 g/m² to about 25 g/m². An example of such a nonwoven material is commercially available under the tradename P-8 from Veratec, Incorporation, a division of the International Paper Company located in Walpole, Mass.

Topsheet 72 can comprise one layer, but in a another embodiment comprises at least two layers. Either layer can be a film, a nonwoven, but in a preferred embodiment, both layers are nonwoven webs. Layered webs can be joined by adhesive, thermal bonding, ultrasonic bonding and the like, but are preferably joined without the use of adhesive or other forms of bonding. Layered webs of topsheet 72 can be joined by interlocking mechanical engagement resulting from the formation of tufts 86 by selective mechanical deformation as taught in U.S. Ser. No. 60/581,483, filed Jun. 21, 2004. Tufts are formed by urging fibers out-of-plane in the Z-direction at discrete, localized, portions of the topsheet. As shown in FIG. 5, topsheet 72 can comprise at least one, but preferably a plurality of, discrete tufts 86 which can be integral extensions of the fibers of the constituent nonwoven webs making up the topsheet 72. For example, if two webs are used as precursor webs, tufts from a first precursor web can extend through a second precursor web to form tufts 86 such that fibers from the first precursor web are disposed on both sides of the topsheet. Each tuft 86 can comprise a plurality of looped, aligned fibers extending outwardly from the body facing surface 70A. In another embodiment each tuft 86 can comprise a plurality of non-looped fibers that extend outwardly from the first body facing surface 70A.

Therefore, from the above description, it is understood that in one embodiment topsheet 72 can be described as being a laminate web formed by selective mechanical deformation of at least a first and second precursor webs, at least the first precursor web being a nonwoven web, the laminate web having a first side, the first side comprising the second precursor web and a plurality of discrete tufts, each of the discrete tufts comprising a plurality of tufted fibers being integral extensions of the first precursor web and extending through the second precursor web; and a second side, the second side comprising the first precursor web.

B. Backsheet:

The absorbent article 1 of FIG. 1 suitable for transfer and/or migration of the skin care compositions of the present invention may also comprise a backsheet that is shown as reference numeral 4. The backsheet 4 can be any known or otherwise effective backsheet material, provided that the backsheet 4 prevents external leakage of exudates absorbed and contained in an absorbent article described herein. Flexible materials suitable for use as the backsheet include, but are not limited to, woven and nonwoven materials, laminated tissue, polymeric films such as thermoplastic films of polyethylene and/or polypropylene, composite materials such as a film-coated nonwoven, material, or combinations thereof.

C. Absorbent Core:

The absorbent article 1 of FIG. 1 also comprises an absorbent core that is shown as reference numeral 5. In an absorbent article of the present invention such as absorbent article 1, the absorbent core 5 is typically positioned between the topsheet 3 and the backsheet 4. As used herein, the term "absorbent core" refers to a material or combination of materials suitable for absorbing, distributing, and storing aqueous fluids such as urine, blood, menses, and water found in body exudates. The size and shape of the absorbent core 5 can be altered to meet absorbent capacity requirements, and to provide comfort to the wearer/user. The absorbent core 5 suitable for use herein can be any liquid-absorbent material known in the art for use in absorbent articles, provided that the liquid-absorbent material can be configured or constructed to meet absorbent capacity requirements. Nonlimiting examples of liquid-absorbent materials suitable for use as the absorbent core 5 herein include comminuted wood pulp which is generally referred to as airfelt; creped cellulose wadding; absorbent gelling materials including superabsorbent polymers such as hydrogel-forming polymeric gelling agents; chemically stiffened, modified, or cross-linked cellulose fibers; meltblown polymers including coform; synthetic fibers including crimped polyester fibers; tissue including tissue wraps and tissue laminates; capillary channel fibers; absorbent foams; absorbent sponges; synthetic staple fibers; peat moss; or any equivalent material; or combinations thereof.

In one embodiment, sanitary napkin 70 comprises a high capacity and highly absorbent core 74. In general, a preferred absorbent core is an airlaid core of the type disclosed in U.S. Pat. No. 5,445,777; or U.S. Pat. No. 5,607,414. In a preferred embodiment, absorbent core 204 is the type generally referred to as HIPE foams, such as those disclosed in U.S. Pat. No. 5,550,167; U.S. Pat. No. 5,387,207; U.S. Pat. Nos. 5,352, 711; and 5,331,015. In a preferred embodiment, absorbent core 74 has a capacity after desorption at 30 cm of less than about 10% of its free absorbent capacity; a capillary absorption pressure of from about 3 to about 20 cm; a capillary desorption pressure of from about 8 to about 25 cm; a resistance to compression deflection of from about 5 to about 85% when measured under a confining pressure of 0.74 psi; and a free absorbent capacity of from about 4 to 125 grams/gram. Each of these parameters can be determined as set forth in U.S. Pat. No. 5,550,167. issued Aug. 27, 1996 to DesMarais. One advantage of utilizing the airlaid or HIPE foam cores as disclosed is that the absorbent core can be made very thin. For example, an absorbent core of the present invention can have an average caliper (thickness) of less than about 3 mm, or less than about 2 mm, and the thickness can be less than about 1 mm.

IV. Methods of Treating the Skin:

The present invention also relates to methods of treating the skin with the skin care compositions described herein. Generally, a safe and effective amount of the skin care composition is applied to an absorbent article described herein wherein such safe and effective amounts include applying from about 0.0015 Mg/cm² (0.01 mg/in²) to about 15.5 mg/cm² (100 mg/in²), preferably from about 0.003 mg/cm² (0.02 mg/in²) to about 12.4 mg/cm² (80 mg/in²), more preferably from about 0.02 mg/cm² (0.015 mg/in²) to about 7.75 mg/cm² (50 mg/in²), of the skin care composition to the absorbent article.

Typically, a safe and effective amount of the skin care compositions of the present invention is applied to an absorbent article such that at least about 0.00015 mg/cm² (0.001 mg/in²) to about 15.5 mg/cm² (100 mg/in²), preferably from about 0.0006 mg/cm² (0.004 mg/in²) to about 11 mg/cm² (72 mg/in²), more preferably from about 0.005 mg/cm² (0.03 mg/in²) to about 6.2 mg/cm² (40 mg/in²), of the composition is transferred to the skin during a single use of an absorbent article which is typically about a three hour period. Absorbent articles are generally changed every three to six hours during the day and once for overnight protection, resulting in at least a safe and effective amount of from about 0.00045 mg/cm² (0.003 mg/in²) to about 124 mg/cm² (800 mg/in²), preferably from about 0.0018 mg/cm$^2$ (0.012 mg/in$^2$) to about 88 mg/cm$^2$ (576 mg/in$^2$), more preferably from about 0.015 mg/cm$^2$ (0.09 mg/in$^2$) to about 49.6 mg/cm$^2$ (320 mg/in$^2$), of the skin care composition being administered within a one day interval (24 hour period). However, the transfer of the skin care compositions of the present invention onto a wearer's skin via an absorbent article described herein can occur for one day, several days, weeks, months, or years at appropriate intervals provided that safe and effective amounts of the skin care compositions are administered to deliver the skin treatment benefits described herein.

The skin care compositions of the present invention can be applied to the absorbent articles by any known or otherwise effective technique for distributing a skin care composition onto an absorbent product such as a disposable absorbent article. Nonlimiting examples of methods of applying the skin care compositions onto an absorbent article include spraying, printing (e.g., flexographic printing), coating (e.g., contact slot coating and gravure coating), extrusion, or combinations of these application techniques. The application of the skin care compositions onto an absorbent article facilitates the transfer or migration of the skin care compositions onto the skin for administration and/or deposition of the skin care compositions, resulting in a safe and effective amount of the compositions being applied for improved prevention and reduction of skin disorders. Therefore, the safe and effective amount of the skin care composition that will transfer or migrate to the skin will depend on factors such as the type of skin care composition that is applied, the portion of the body contacting surface where the skin care composition is applied, and the type of absorbent article used to administer the skin care composition.

Any suitable method can be used in determining the amount of a skin care composition described herein that is transferred to the skin of a wearer during use of an absorbent article containing the composition. An example of specific methods for the calculation of transfer amounts of skin care compositions include Gas Chromatographic and other quantitative analytical procedures that involve the analysis of in vivo skin analog materials. A suitable Gas Chromatographic procedure is more fully described in WO 99/45973, Donald C. Roe et al, published Sep. 16, 1999.

V. Method of Manufacture:

The skin care compositions of the present invention may be prepared by any known or otherwise effective technique, suitable for providing a skin care composition comprising the essential skin treatment agents defined herein. In general, the skin care compositions are prepared by first making a carrier system comprising suitable carriers such as petrolatum, behenyl alcohol, and beheneth-10 in combination with a fumed silica thickening agent. Next, a mixture comprising the skin treatment agents and any optional ingredients such as optional skin conditioning agents are added to the carrier system at a melt mix temperature of about 80° C. Although the carrier system, skin treatment agents, and any optional ingredients are typically processed at a temperature of about 80° C., these materials can be processed at temperatures ranging from about 60° C. to about 90° C., preferably from about 70° C. to about 90° C. The resultant skin care composition is subsequently applied to a topsheet component of an absorbent article using a contact applicator such as a Meltex EP45 hot melt applicator.

The skin care compositions of the present invention are prepared such that the compositions can be applied to an absorbent article to result in safe and effective amounts of the compositions being transferred onto the skin of a wearer of the absorbent article. Therefore, the skin care compositions preferably have a product consistency such that they are relatively immobile and localized on the wearer-contacting surface of the absorbent article at ambient conditions, are readily transferable to the wearer at body temperature, and yet are not completely liquid under extreme storage conditions. In other words, the skin care compositions are solids or semisolids at ambient conditions (about 25° C.) and/or body temperature (about 37° C.) so that the compositions are easily transferred onto the skin by way of normal contact, wearer motion, and/or body heat. The consistency of the skin care compositions can be measured according to ASTM D5 test method which involves the use of a penetrometer to measure consistency. Typically, the skin care compositions of the present invention have a consistency of from about 10 to about 300, preferably from about 20 to about 250, more preferably from about 30 to about 200, as measured at 40° C. according to the test procedure outlined in ASTM D5 test method.

The solid or semisolid consistency of the skin care compositions provide for relatively low levels of the compositions to be applied to the absorbent articles to impart the desired skin care benefits. By "semisolid" is meant that the compositions have a rheology typical of pseudoplastic or plastic liquids such that the compositions remain relatively stationary in a desired location on the absorbent article, and do not have a tendency to flow or migrate to undesired locations of the article. The solid skin care compositions of the present invention likewise can remain in a particular location and not flow or migrate to undesired locations of the article. These solid and semisolid skin care compositions have viscosities high enough to keep the compositions localized on an intended location of the article, but not so high as to impede transfer to the wearer's skin. Typically, final products of solid and semisolid skin care compositions have viscosities ranging from about $1.0 \times 10^6$ centipoise to about $1.0 \times 10^{10}$ centipoise under shear stress conditions of about $3 \times 10^3$ dynes/cm$^2$ at 40° C. (the shear stress applied to the compositions while the absorbent article is in storage or transported at temperature conditions of about 40° C.).

However, the solid and semisolid skin care compositions can be made flowable for transfer or migration of the compositions onto the skin by applying shear stress that results in deformation of the compositions. The shear stress applied at least once during wear of the absorbent article under temperature conditions of about 40° C. is typically at about $1.0 \times 10^6$ dynes/cm$^2$, and this shear stress can result in the skin care compositions having a viscosity of from about $1.0 \times 10^1$ centipoise to about $1.0 \times 10^5$ centipoise. It is believed that the skin care compositions achieve the lower viscosity values under applied shear stress due to the fact that, while the compositions contain solid components, they also contain liquid materials. During wear of an absorbent article described herein, it is desirable to achieve a low viscosity for obtaining sufficient lubrication between the wearer's skin and the body contacting surface of the article to result in effective transfer of the skin care composition onto the wearer's skin. Viscosity at various shear stress can be measured using rheometers known in the art such as the Rheometer SR-2000 available from Rheometrics Incorporation.

The skin care compositions are typically applied to the topsheet of an absorbent article for delivery of the skin care composition onto an external or internal surface of the skin. The skin care composition can be applied to other areas of the absorbent article wherein these areas include wings, side panels, the absorbent core, any secondary layer intermediate the core and topsheet, or any other region of the absorbent article.

Processes for assembling absorbent articles such as the disposable absorbent articles described herein include conventional techniques known in the art for constructing and configuring disposable absorbent articles. For example, the backsheet and/or the topsheet can be joined to the absorbent core or to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL-1258 or H-2031.

The skin care compositions of the present invention can also be delivered onto the skin by incorporating the compositions into aerosol dispensers, trigger spray dispensers, pump spray dispensers, jars, stick dispensers, cotton balls, patches, sponges, and any other type of known or otherwise effective delivery vehicle.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. All exemplified concentrations are weight-weight percents, unless otherwise specified.

Example I

The compositions exemplified hereinbelow in Table 1 are representative of carrier systems of the skin care compositions of the present invention. The carrier systems are generally prepared by combining, by weight, petrolatum and a fatty alcohol such as behenyl alcohol, and then heating the mixture while stirring to a temperature of about 80° C. using a low speed propeller mixer. Next, viscosity or thickening agents are added to the mixture to shear mix the ingredients into a final carrier system. Suitable viscosity or thickening agents include beheneth-10, fumed silica, bentonite, and steareth-2, wherein the viscosity or thickening agents are used alone or in combination. The ingredients can be shear mixed at 11,000 revolutions per minute (rpm) using an IKA Ultra Turrax Shear Mixer.

Alternatively, the petrolatum, fatty alcohol, and viscosity or thickening agent can be combined, heated with stirring at 80° C. to melt the ingredients, and then mixed into a final carrier system using a high speed blade mixer such as the Tokusyu Kika TK Robo Mics which operates at 5,000 rpm.

TABLE 1

Carrier Systems

| Component | Sample 1 (Wt. %) | Sample 2 (Wt. %) | Sample 3 (Wt. %) | Sample 4 (Wt. %) | Sample 5 (Wt. %) |
|---|---|---|---|---|---|
| Petrolatum[1] | 78.1 | 67.8 | 70.0 | 70.0 | 70.0 |
| Behenyl Alcohol[2] | 8.7 | 29.0 | — | 20.0 | 15.0 |
| Cetearyl Alcohol[3] | — | — | 30.0 | — | — |
| Beheneth-10[4] | 10.0 | — | — | — | — |
| Fumed Silica[5] | 3.2 | 3.2 | — | — | — |
| Bentonite[6] | — | — | — | 10.0 | — |
| Steareth-2[7] | — | — | — | — | 15.0 |

Wt. %-weight percent
[1] petrolatum available as Protopet ® 1S from the Witco Corporation
[2] behenyl alcohol available as Lanette 22 from the Cognis Corporation
[3] cetearyl alcohol available as Stenol 1822 from the Cognis Corporation
[4] beheneth-10 available as Mergital ® B10 from the Cognis Corporation
[5] fumed silica available as Cabosil ® TS-720 from the Cabot Corporation
[6] bentonite available as Bentone ® 38 from the Rheox Incorporation
[7] steareth-2 available as Brij ® 762 from the Uniqema Corporation

Examples II-IX

The following Examples II-IX illustrated hereinbelow in Table 2 are representative of skin care compositions of the present invention that include the carrier systems identified in Table 1. The skin care compositions are prepared by formulating a premix solution of the zinc oxide skin treatment agent and adding the zinc oxide premix to the other skin treatment agents and any optional ingredients such as panthenol and glycerin, or by formulating a skin treatment solution of hexamidine and niacinamide skin treatment agents and any optional ingredients. The skin treatment solution is then added to a carrier system such as those described in Table 1, wherein the skin treatment solution and carrier system is heated while stirring to a temperature of about 80° C. All ingredients are included by weight of the skin care compositions. These skin care compositions are especially effective in the control of skin disorders such as skin erythema, malodor, and skin bacterial infections.

TABLE 2

Skin Care Compositions

| Component | Ex. II (Wt. %) | Ex. III (Wt. %) | Ex. IV (Wt. %) | Ex. V (Wt. %) | Ex. VI (Wt. %) | Ex. VII (Wt. %) | Ex. VIII (Wt. %) | Ex IX (Wt. %) |
|---|---|---|---|---|---|---|---|---|
| Sample 1 | 97.1 | 98.1 | 89.8 | — | — | — | — | — |
| Sample 2 | — | — | — | 96.2 | 99.7 | — | — | — |
| Sample 3 | — | — | — | — | — | 95.7 | — | — |
| Sample 4 | — | — | — | — | — | — | 97.3 | — |
| Sample 5 | — | — | — | — | — | — | — | 97.8 |
| ZnO Premix[8] | 0.7 | 0.2 | 7.1 | 0.75 | 0.2 | — | — | — |
| Hexamidine[9] | 0.1 | 0.1 | 0.1 | 0.05 | 0.1 | 0.1 | 0.05 | 0.1 |
| Panthenol[10] | 0.5 | 0.5 | 0.5 | 0.5 | — | 0.5 | 0.25 | — |
| Glycerine[11] | 0.1 | 0.1 | — | — | — | — | — | 0.1 |
| Niacinamide[12] | 1.0 | 1.0 | 2.0 | 2.0 | — | — | — | 2.0 |

TABLE 2-continued

Skin Care Compositions

| Component | Ex. II (Wt. %) | Ex. III (Wt. %) | Ex. IV (Wt. %) | Ex. V (Wt. %) | Ex. VI (Wt. %) | Ex. VII (Wt. %) | Ex. VIII (Wt. %) | Ex IX (Wt. %) |
|---|---|---|---|---|---|---|---|---|
| Acidified Niacinamide[13] | — | — | — | — | — | 3.7 | 1.9 | — |
| Chamomile[14] | 0.5 | — | 0.5 | 0.5 | — | — | 0.5 | — |

[8]Zinc oxide premix comprising 70% zinc oxide mixture of ULTRAFINE 350 zinc oxide available from the Kobo Incorporation, Arlecel ® P100 available from the Uniqema Incorporation, and Salacos ® 99 available from the Ikeda Incorporation
[9]hexamidine available as hexanildine diisetbionate from Laboratories Serolobilogiques under the tradename ELASTAB HP 100
[10]panthenol available as D-panthenol from Roche Vitamins Incorporation
[11]glycerine available as Glycerine, USP Kosher ® from the Procter & Gamble Company
[12]niacinamide available from Em Industries HHN
[13]acidified niacinamide made by reacting niacinamide with stearic acid
[14]chamomile available as Phytoconcentrol Chamomile from Dragoco The skin care composition of Example II is subsequently applied to the entire wearer-contacting surface of a DRI-WEAVE topsheet of a sanitary pad product such as Allways Wing Regular Long manufactured by the Procter & Gamble Company. To deliver a safe and effective amount of the skin care composition onto the skin, about 0.4 mg/cm$^2$ (2.6 mg/in$^2$) of the skin care composition is applied to the topsheet using a Meltex EP45 hot melt applicator having a head operating temperature of about 90° C.

The skin care composition of Example III is subsequently applied by spraying the composition onto the entire wearer-contacting surface of a DRI-WEAVE topsheet of a sanitary pad product such as Envive Miniform manufactured by the Procter & Gamble Company. To deliver a safe and effective amount of the skin care composition onto the skin, about 4.0 mg/cm$^2$ (25.8 mg/in$^2$) of the skin care composition is applied to the topsheet using a hot melt pneumatic Dynatec E84B1758 spray head having a head operating temperature of about 90° C. and an atomization pressure of about 16 kiloPascals (kPa).

The skin care composition of Example IV is subsequently applied by spraying striped configurations of the composition onto the wearer-contacting surface of a DRI-WEAVE topsheet of a sanitary pad product such as Always Wing Regular Long manufactured by the Procter & Gamble Company. To deliver a safe and effective amount of the skin care composition onto the skin, the skin care composition is applied to the topsheet in a striped configuration wherein the striped configuration comprises at least two stripes each being 40 millimeters (mm) wide×200 mm long and having about 0.8 mg/cm$^2$ (5.2 mg/in) of the composition applied thereon. The skin care composition is applied to the topsheet using a hot melt pneumatic Dynatec E84B1758 spray head having a head operating temperature of about 90° C. and an atomization pressure of about 16 kiloPascals (kPa).

The skin care composition of Example V is subsequently applied by spraying striped configurations of the composition onto the wearer-contacting surface of a DRI-WEAVE topsheet of a panty liner product such as Alldays Regular manufactured by the Procter & Gamble Company. To deliver a safe and effective amount of the skin care composition onto the skin, the skin care composition is applied to the topsheet in a striped configuration wherein the striped configuration comprises at least two stripes each being 40 millimeters (mm) wide×200 mm long and having about 0.6 mg/cm$^2$ (3.9 mg/in$^2$) of the composition applied thereon. The skin care composition is applied to the topsheet using a hot pneumatic Dynatec E84B1758 spray head having a head operating temperature of about 90° C. and an atomization pressure of about 16 kiloPascals (kPa).

The skin care composition of Example VI is subsequently applied to the entire wearer-contacting surface of a DRI-WEAVE topsheet of a panty liner product such as Alldays Regular manufactured by the Procter & Gamble Company. To deliver a safe and effective amount of the skin care composition onto the skin, about 0.2 mg/cm$^2$ (1.3 mg/in$^2$) of the skin care composition is applied to the topsheet using a Meltex EP45 hot melt applicator having a head operating temperature of about 90° C.

The skin care composition of Example VII is subsequently applied by spraying the composition onto the entire wearer-contacting surface of a DRI-WEAVE topsheet of sanitary pad product such as Envive Miniform manufactured by the Procter & Gamble Company. To deliver a safe and effective amount of the skin care composition onto the skin, about 1.0 mg/cm$^2$ (6.5 mg/in$^2$) of the skin care composition is applied to the topsheet using a hot melt pneumatic Dynatec E84B1758 spray head having a head operating temperature of about 90° C. and an atomization pressure of about 16 kiloPascals (kPa).

The skin care composition of Example VIII is subsequently applied to the entire wearer-contacting surface of a DRI-WEAVE topsheet of a panty liner product such as Alldays Regular manufactured by the Procter & Gamble Company. To deliver a safe and effective amount of the skin care composition onto the skin, about 0.4 mg/cm$^2$ (2.6 mg/in$^2$) of the skin care composition is applied to the topsheet using a Meltex EP45 hot melt applicator having a head operating temperature of about 90° C.

The skin care composition of Example IX is subsequently applied by spraying the composition onto the entire wearer-contacting surface of a DRI-WEAVE topsheet of a sanitary pad product such as Envive Miniform manufactured by the Procter & Gamble Company or onto the entire wearer-contacting surface of a DRI-WEAVE topsheet of a hemorrhoid patch. To deliver a safe and effective amount of the skin care composition onto the skin, about 3.0 mg/cm$^2$ (19.5 mg/in$^2$) of the skin care composition is applied to the topsheet using a hot melt pneumatic Dynatec E84B1758 spray head having a head operating temperature of about 90° C. and an atomization pressure of about 16 kiloPascals (kPa).

All documents cited are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A sanitary napkin comprising:
   a topsheet;
   a backsheet;
   an absorbent core disposed between the topsheet and backsheet; and
   a skin care composition applied on the topsheet;
   wherein the topsheet comprises a first layer comprising a nonwoven, a second layer adjacent the first layer, and a plurality of fiber tufts comprising integral extensions of fibers from the nonwoven that extend into and/or through the second layer; and wherein the first layer and second layer are joined by adhesive, ultrasonic bonding, interlocking mechanical engagement, and/or combinations thereof.

2. The sanitary napkin of claim 1, wherein said caliper is less than about 2.0 mm.

3. The sanitary napkin of claim 1, wherein said sanitary napkin comprises a topsheet, and said skin care composition is applied to said topsheet on an area at least one square centimeter in an amount of 0.0015 mg/cm$^2$ to 15.5 mg/cm$^2$.

4. The sanitary napkin of claim 1, wherein said sanitary napkin comprises a topsheet, and said skin care composition is applied to said topsheet in an amount of 0.02 mg/cm$^2$ to 7.75 mg/cm$^2$.

5. The sanitary napkin of claim 1, wherein said skin care composition comprises an antimicrobial agent.

6. The sanitary napkin of claim 1 wherein said composition comprises 60% to 99.9% by weight of the carrier wherein the carrier is selected from the group consisting of petroleum-based hydrocarbons having 4 to 32 carbon atoms, fatty alcohols having 12 to 24 carbon atoms, lower alcohols having 1 to 6 carbon atoms, low molecular weight glycols and polyols, lanolin, and mixtures thereof.

7. The sanitary napkin of claim 1 wherein the skin care composition further comprises 0.001% to 10% by weight of a skin conditioning agent selected from the group consisting of panthenol, glycerine, and mixtures thereof.

8. The sanitary napkin of claim 1 wherein the composition further comprises a skin treatment active selected from the group consisting of allantoin, aluminum hydroxide gel, calamine, cysteine hydrochloride, racemic methionine, sodium bicarbonate, Vitamin C and derivatives thereof, serine protease, metalloprotease, cysteine protease, aspartyl protease, peptidase, phenylsulfonyl fluoride, lipase, diesterase, urease, amylase, elastase, nuclease, guanidinobenzoic acid and its salts and derivatives, chamomile, and mixtures thereof.

9. A method of reducing skin disorders comprising the steps of:
   a. wearing an absorbent article having a caliper of less than 5 mm; wherein the absorbent article comprises a topsheet having a first layer, a second layer, and integral fiber tufts extending from the first layer and through the second layer, at least some of the fiber tufts comprising a skin care composition; and
   b. transferring at least a portion of the skin care composition to an external skin surface via movement of the fiber tufts against the skin.

10. The method of claim 9 wherein the absorbent article comprises 0.0015 mg/cm$^2$ to 15.5 mg/cm$^2$ of the skin care composition and wherein 0.00045 mg/cm$^2$ to 124 mg/cm$^2$ of the skin care composition is transferred onto the external skin surface within a 24 hour period.

11. A sanitary napkin for wearing adjacent the pudendal region, said sanitary napkin comprising a topsheet, a backsheet joined to the topsheet, wings, and an absorbent core disposed between the topsheet and backsheet, said topsheet comprising a first layer, a second layer, and at least one integral discrete fiber tuft, wherein said sanitary napkin comprises a skin care composition, wherein said sanitary napkin has a caliper less than 5.0 mm, and wherein the at least one integral discrete fiber tuft extends from within the first layer and through the second layer of the topsheet.

12. The sanitary napkin of claim 11, wherein said tuft extends out-of-plane in the Z-direction with respect to the sanitary napkin.

13. The sanitary napkin of claim 11, wherein said caliper is less than 2.0 mm.

14. The sanitary napkin of claim 11, wherein said skin care composition is applied to said topsheet in an amount of 0.0015 mg/cm$^2$ to 15.5 mg/cm$^2$.

15. The sanitary napkin of claim 1, wherein said caliper is less than about 3.0 mm.

16. The sanitary napkin of claim 1, wherein the skin care composition is hydrophobic.

17. The sanitary napkin of claim 1, wherein the topsheet second layer comprises a film.

18. The sanitary napkin of claim 1, wherein the topsheet second layer comprises a second nonwoven.

19. The sanitary napkin of claim 1, wherein the skin care composition comprises at least one of hexamidine, zinc oxide, and niacinamide.

20. The sanitary napkin of claim 1, wherein the skin care composition comprises:
   a. 0.001% to 0.1% by weight of hexamidine;
   b. 0.001% to 10% by weight of zinc oxide;
   c. 0.01% to 10% by weight of niacinamide; and
   a carrier.

* * * * *